United States Patent
Tsai et al.

(10) Patent No.: US 9,669,213 B2
(45) Date of Patent: Jun. 6, 2017

(54) STIMULATION METHOD FOR MAINTAINING THE RESPONSIVENESS OF ELECTRICALLY EXCITABLE CELLS TO REPEATED ELECTRICAL STIMULATION

(76) Inventors: David Tsai, West Pennant Hills (AU);
John William Morley, Blaxland (AU);
Gregg Jorgen Suaning, Lisarow (AU);
Nigel Hamilton Lovell, Coogee (AU)

( * ) Notice: Subject to any disclaimer, the term of this patent is extended or adjusted under 35 U.S.C. 154(b) by 0 days.

(21) Appl. No.: 13/981,584

(22) PCT Filed: Jan. 24, 2012

(86) PCT No.: PCT/AU2012/000055
§ 371 (c)(1),
(2), (4) Date: Jul. 24, 2013

(87) PCT Pub. No.: WO2012/100290
PCT Pub. Date: Aug. 2, 2012

(65) Prior Publication Data
US 2013/0310899 A1    Nov. 21, 2013

Related U.S. Application Data

(60) Provisional application No. 61/435,696, filed on Jan. 24, 2011.

(51) Int. Cl.
*A61N 1/36* (2006.01)
*A61N 1/05* (2006.01)

(52) U.S. Cl.
CPC ....... *A61N 1/36046* (2013.01); *A61N 1/0543* (2013.01)

(58) Field of Classification Search
CPC .... A61N 1/36; A61N 1/36046; A61N 1/3605; A61N 1/05; A61N 1/0529; A61N 1/0543
USPC .......................... 607/48, 52, 53, 62, 68, 116
See application file for complete search history.

(56) References Cited

U.S. PATENT DOCUMENTS

| | | | | |
|---|---|---|---|---|
| 5,222,494 | A | * | 6/1993 | Baker, Jr. ..................... 607/118 |
| 5,318,572 | A | * | 6/1994 | Helland et al. ............... 607/121 |
| 5,501,703 | A | * | 3/1996 | Holsheimer et al. ........... 607/46 |
| 6,226,551 | B1 | * | 5/2001 | Zhu et al. ........................ 607/28 |
| 6,292,693 | B1 | * | 9/2001 | Darvish et al. .................. 607/9 |
| 6,458,157 | B1 | * | 10/2002 | Suaning ..................... 623/6.63 |
| 6,561,968 | B1 | * | 5/2003 | Dissing et al. ................ 600/13 |
| 6,594,525 | B1 | | 7/2003 | Zierhofer |
| 6,690,974 | B2 | | 2/2004 | Archer et al. |

(Continued)

OTHER PUBLICATIONS

NewSouth Innovations Pty Limited, Extended European Search Report, App No. 12739096.1, Jul. 2, 2014, 9 pgs.

(Continued)

*Primary Examiner* — Christopher A Flory
(74) *Attorney, Agent, or Firm* — Morgan, Lewis & Bockius LLP (57) ABSTRACT

A method of neural stimulation is described for maintaining the responsiveness of electrically excitable cells to repeated electrical stimulation. A stimulating signal (23) is applied to the electrically excitable cells. The stimulating signal is repeatedly applied (26, 29, 32, 35) with a progressively increasing signal strength. A quiescent period (44) may be interleaved between bursts (43, 45) of stimulation. The electrically excitable cells may be retinal cells.

18 Claims, 6 Drawing Sheets

(56) References Cited

U.S. PATENT DOCUMENTS

| | | | |
|---|---|---|---|
| 7,118,217 B2* | 10/2006 | Kardon | A61B 3/0058 351/206 |
| 7,571,004 B2 | 8/2009 | Roy et al. | |
| 7,765,009 B2 | 7/2010 | Greenberg et al. | |
| 8,003,372 B2* | 8/2011 | Klauke et al. | 435/285.2 |
| 2002/0077670 A1 | 6/2002 | Archer et al. | |
| 2005/0125043 A1* | 6/2005 | Tass | 607/45 |
| 2005/0277099 A1* | 12/2005 | Van Schaack et al. | 434/322 |
| 2006/0003310 A1* | 1/2006 | Klauke et al. | 435/4 |
| 2006/0161218 A1* | 7/2006 | Danilov | A61B 5/0492 607/45 |
| 2006/0167500 A1* | 7/2006 | Towe et al. | 607/3 |
| 2006/0167528 A1 | 7/2006 | Roy et al. | |
| 2006/0212089 A1* | 9/2006 | Tass | 607/45 |
| 2007/0048731 A1* | 3/2007 | Colicos et al. | 435/4 |
| 2007/0067003 A1* | 3/2007 | Sanchez | A61N 1/36082 607/45 |
| 2007/0135860 A1* | 6/2007 | Tass | 607/45 |
| 2007/0156202 A1 | 7/2007 | Zierhofer | |
| 2007/0203532 A1* | 8/2007 | Tass et al. | 607/45 |
| 2008/0045856 A1 | 2/2008 | Horsager et al. | |
| 2008/0125832 A1 | 5/2008 | Horsager et al. | |
| 2008/0242588 A1* | 10/2008 | Xiong | C40B 30/06 514/1.1 |
| 2009/0024189 A1 | 1/2009 | Lee et al. | |
| 2009/0076561 A1* | 3/2009 | Libbus | A61N 1/36114 607/11 |
| 2009/0088680 A1* | 4/2009 | Aravanis et al. | 604/21 |
| 2009/0093403 A1* | 4/2009 | Zhang et al. | 514/12 |
| 2009/0112133 A1* | 4/2009 | Deisseroth et al. | 601/3 |
| 2009/0132004 A1 | 5/2009 | Greenberg et al. | |
| 2009/0228078 A1* | 9/2009 | Zhang | A61B 5/4035 607/62 |
| 2009/0306741 A1* | 12/2009 | Hogle | A61N 1/36082 607/54 |
| 2009/0312808 A1* | 12/2009 | Tyler | A61B 5/0492 607/2 |
| 2009/0312817 A1* | 12/2009 | Hogle | A61B 5/0492 607/54 |
| 2009/0312818 A1 | 12/2009 | Horsager et al. | |
| 2010/0190229 A1* | 7/2010 | Zhang et al. | 435/173.1 |
| 2010/0262205 A1* | 10/2010 | De Ridder | A61N 1/3605 607/17 |
| 2011/0077722 A1* | 3/2011 | Towe et al. | 607/68 |
| 2011/0106206 A1* | 5/2011 | Schiff | 607/45 |
| 2011/0137373 A1* | 6/2011 | Tass | 607/45 |
| 2011/0152967 A1* | 6/2011 | Simon | A61N 1/40 607/45 |
| 2011/0159562 A1* | 6/2011 | Deisseroth | A61N 5/0601 435/173.8 |
| 2011/0172653 A1* | 7/2011 | Schneider et al. | 606/15 |
| 2011/0212090 A1* | 9/2011 | Pedersen | A61K 39/0011 424/133.1 |
| 2011/0224749 A1* | 9/2011 | Ben-David | A61N 1/36071 607/9 |
| 2011/0269235 A1* | 11/2011 | Rawson | C12N 5/062 435/456 |
| 2012/0004707 A1* | 1/2012 | Lee | A61N 1/36017 607/59 |
| 2012/0041499 A1* | 2/2012 | Towe et al. | 607/3 |
| 2012/0078319 A1* | 3/2012 | De Ridder | A61N 1/3605 607/9 |
| 2012/0108640 A1* | 5/2012 | Hochman | A61K 31/18 514/347 |
| 2012/0143080 A1* | 6/2012 | Greenberg | A61B 3/0025 600/554 |
| 2012/0221075 A1* | 8/2012 | Bentwich | A61B 5/0476 607/45 |
| 2013/0190840 A1* | 7/2013 | Libbus | A61N 1/36114 607/59 |
| 2013/0231713 A1* | 9/2013 | De Ridder | A61N 1/3605 607/42 |
| 2013/0245486 A1* | 9/2013 | Simon | A61N 1/36021 600/546 |
| 2013/0245713 A1* | 9/2013 | Tass | 607/45 |
| 2013/0245722 A1* | 9/2013 | Ternes | A61N 1/36053 607/62 |
| 2013/0289669 A1* | 10/2013 | Deisseroth et al. | 607/88 |
| 2013/0310899 A1* | 11/2013 | Tsai et al. | 607/62 |
| 2013/0331919 A1* | 12/2013 | Zhang | A61B 5/4035 607/119 |
| 2013/0338727 A1* | 12/2013 | Mokelke | A61N 1/3606 607/45 |
| 2014/0046407 A1* | 2/2014 | Ben-Ezra | A61N 1/0556 607/62 |
| 2014/0128972 A1* | 5/2014 | Khraiche | A61L 27/18 623/6.63 |
| 2014/0203818 A1* | 7/2014 | Wang et al. | 324/603 |
| 2015/0088212 A1* | 3/2015 | De Ridder | A61N 1/0529 607/2 |
| 2015/0290453 A1* | 10/2015 | Tyler | A61N 1/0548 607/134 |

OTHER PUBLICATIONS

NewSouth Innovations Pty Limited, International Search Report and Written Opinion, PCT/AU2012/000055, Apr. 23, 2012, 11 pgs.
Ryu, Temporal Response Properties of Retinal Ganglion Cells in rd1 Mice Evoked by Amplitude-Modulated Electrical Pulse Trains, Investigative Ophthalmology & Visual Science, vol. 51, No. 12, Dec. 2010, pp. 6762-6769.
Talukder, High Resolution Implantable Microsystem and Probe Design for Retinal Prosthesis, The Open Ophthalmology Journal, 2008, vol. 2, pp. 77-90.
Tsai, Frequency-dependent reduction of voltage-gated sodium current modulates retinal ganglion cell response rate to electrical stimulation, IOP Publishing Limited, Oct. 26, 2011, 12 pgs.
NewSouth Innovations Pty Limited, Patent Examination Report No. 2, AU2012211030, May 31, 2016, 4 pgs.

* cited by examiner

STIMULATION METHOD FOR MAINTAINING THE RESPONSIVENESS OF ELECTRICALLY EXCITABLE CELLS TO REPEATED ELECTRICAL STIMULATION

CROSS REFERENCE TO RELATED APPLICATIONS

This application is a United States National Stage Application filed under 35 U.S.C. §371 of PCT Patent Application Serial No. PCT/AU2012/000055 filed on Jan. 24, 2012, which claims the benefit of U.S. provisional patent application No. 61/435,696, filed Jan. 24, 2011, the entire content of which is incorporated herein by reference.

FIELD OF THE INVENTION

The invention relates to the electrical stimulation of electrically excitable cells, and in particular to a method and system for maintaining the responsiveness of the cells to repeated electrical stimulation.

BACKGROUND OF THE INVENTION

Electrical stimulation has been used extensively as a therapeutic treatment for restoring function in disabled individuals. Application examples include but are not limited to retinal implants. Electrical stimulation artificially elicits responses from excitable cells by activating the voltage-gated ion channels present in these cells. To repeatedly evoke responses, a stimulation strategy involves delivering, in quick succession, a train of stimuli, with each stimulus having equal amplitude and duration. However, repeated stimulation within a short period of time could cause the said voltage-gated ion channels to undergo use-dependent inactivation, thus resulting in a decline of electrically evoked response rate.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

The present invention relates to a stimulation method for maintaining the evoked response reliability of excitable cells during repetitive electrical stimulation. In broad terms this is achieved through a progressive increase of the artificial stimulus strength. The train of stimulating pulses may be interleaved with periods of time without stimulus.

According to a first aspect of the invention there is provided a method of neural stimulation for maintaining the responsiveness of electrically excitable cells to repeated electrical stimulation, comprising:

applying a stimulating signal to the electrically excitable cells; and repeating the application of the stimulating signal with a progressively increasing signal strength.

Increasing the signal strength may comprise increasing a total electric charge applied to the cells within a specified time period, for example by increasing an amplitude of the stimulating signal, increasing a pulse duration of the stimulating signal, or increasing a number of pulses applied within a specified time period.

According to a further aspect of the invention there is provided a neural stimulator comprising:

a sensory detection device, such as a camera, that in use detects sensory information;

an electrode array that in use is configured to stimulate electrically excitable cells; and a processing circuit in data communication with the sensory detection device and the electrode array, wherein the processing circuit causes the electrode array to apply a stimulating signal to the electrically excitable cells dependent on the detected sensory data and, if the stimulating signal is repeated, a signal strength of the stimulating signal is increased progressively to maintain responsiveness of the cells to the repeated stimulating signal.

The processing circuit may interleave a quiescent period between a first burst of repeated applications of the stimulating signal and a second burst of repeated applications of the stimulating signal.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

The present invention relates to a stimulation method for maintaining the evoked response reliability of excitable cells during repetitive electrical stimulation. The description relates to retinal stimulation, although it will be understood that the method may also be applied to other electrically excitable cells.

Figure 1:
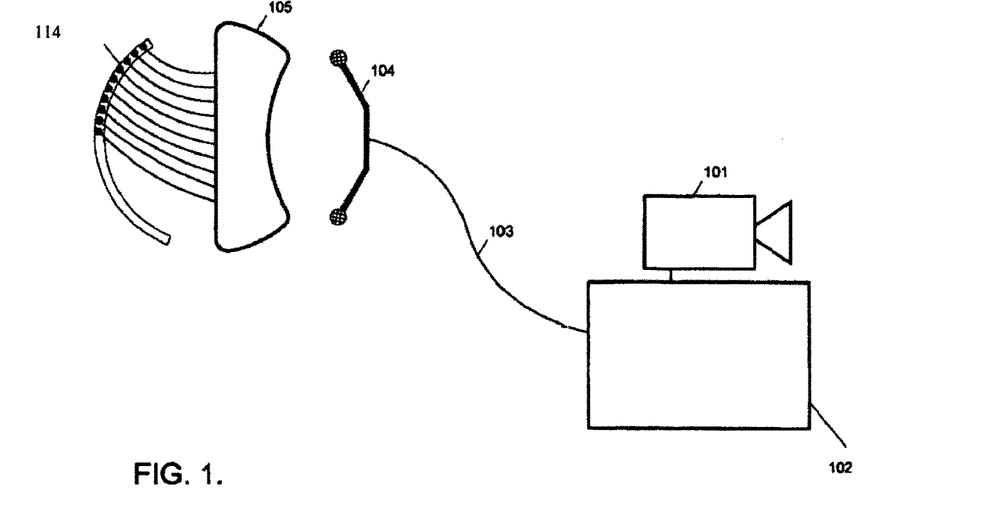
FIG. 1 is a schematic illustration of a retinal stimulation system.

FIG. 1 illustrates a retinal stimulation system that includes an external image detector 101 that supplies an external processing unit 102 with image data. For example, image detector 101 may be a camera system mounted on a pair of glasses worn by a user of the retinal stimulation system. The processor 102 translates the image data into a series of encoded, radiofrequency bursts according to a pre-determined protocol, which the processor provides to a tuned transmitting antenna 104, for example via cable 103. Transmitted radiofrequency waves are broadcast from antenna 104, through tissue (not shown), and received and decoded in the implanted portion 105 of the retinal stimulation system. The implanted electronics extracts stimulation parameter data and rectifies the received signal to power the implanted portion 105. In accordance with the decoded data, a controlled, biphasic, charge balanced stimulus wave is delivered to an active stimulating electrode on electrode array 114, enters retinal tissue (not shown) and returns through one or more indifferent electrode(s) to implanted portion 105.

Figure 2:
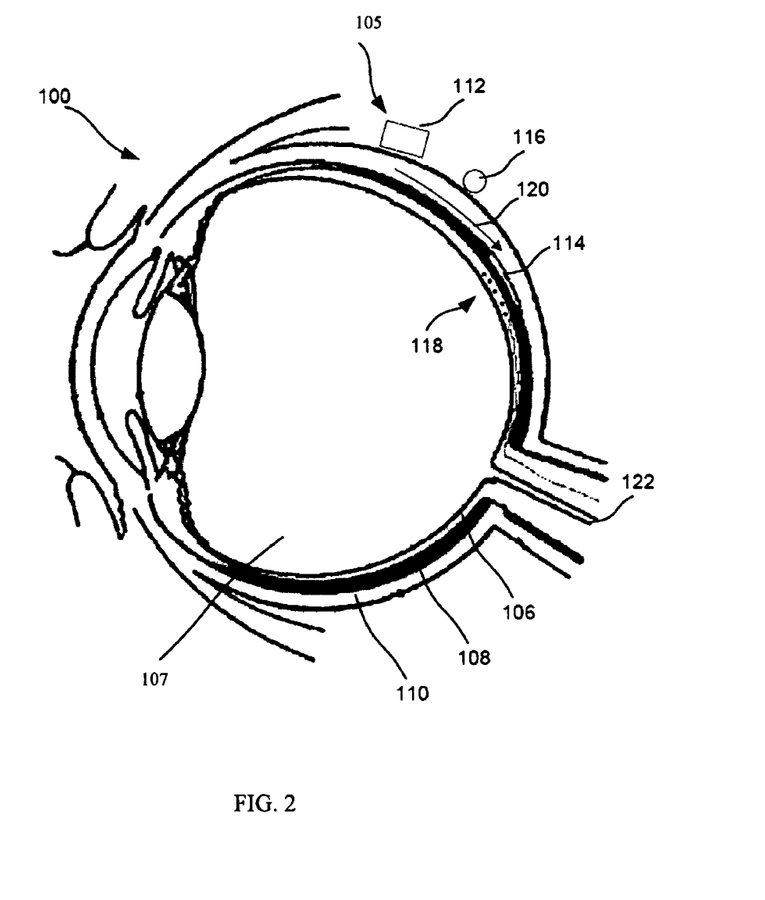
FIG. 2 is a schematic cross-sectional view of an eye with an example of an implanted neural prosthesis.

FIG. 2 shows a cross section of an eye 100 with the implanted portion of a retinal stimulator 105. The eye 100 includes three layers bounding the vitreous humour 107: the neural retina 106, choroid 108 and sclera 110.

The stimulator 105 may include at least one electronics capsule 112, electrode array 114 and a monopolar return electrode 116. When implanting these components of the prosthesis the electrode array 114 is inserted into the eye to be near to the neurons 118 that lie in the neural retina 106 and that need to be stimulated. However, the choroid 108 is the vascular layer of the eye, so incisions may result in unwanted bleeding. Therefore, one method of inserting the electrode array 114 without penetrating the choroid 108 is to make an incision through the sclera 110, for example proximate the electronics capsule 112, and to slide the array along the interface between the sclera 110 and the choroid 108, for example in the direction of arrow 120 until the electrode array is in the desired location, adjacent the necessary neurons 118 but on the opposite side of the choroid 108. In this configuration stimulating pulses from the electrode array 114 may stimulate the neurons 118 from across the choroid.

When signals are transmitted to the eye for neural stimulation, electrical impulses or stimuli are presented to the eye by injecting electrical current from the electrode array 114 into the tissue, and the current is returned to the implant circuitry via one or more of the electrodes in the array 114, and/or the monopolar return electrode 116. In this way the neurons 118 are stimulated so that they contribute to the perception of phosphenes. Information within the neurons 118 passes to the user's brain via the optic nerve 122.

Figure 3:
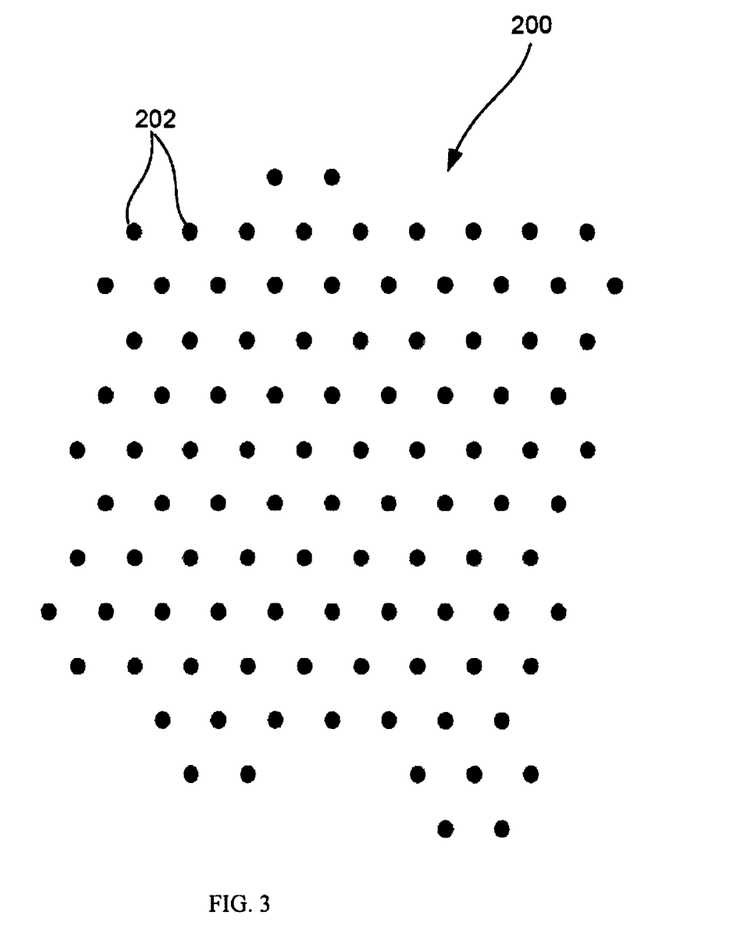
FIG. 3 is a plan view of an example of an electrode array.

A high density of electrodes may provide a high density of phosphenes thereby allowing better visual acuity in the implant recipient. However, if any two regions of activation are too close, injected charge may interfere. Arranging individual electrodes 202 in a staggered geometric array 200 as shown in FIG. 3 allows for high density of phosphenes. When providing stimuli, the electrodes need to be addressed in some way to be able to provide the required stimulus.

Figure 4:
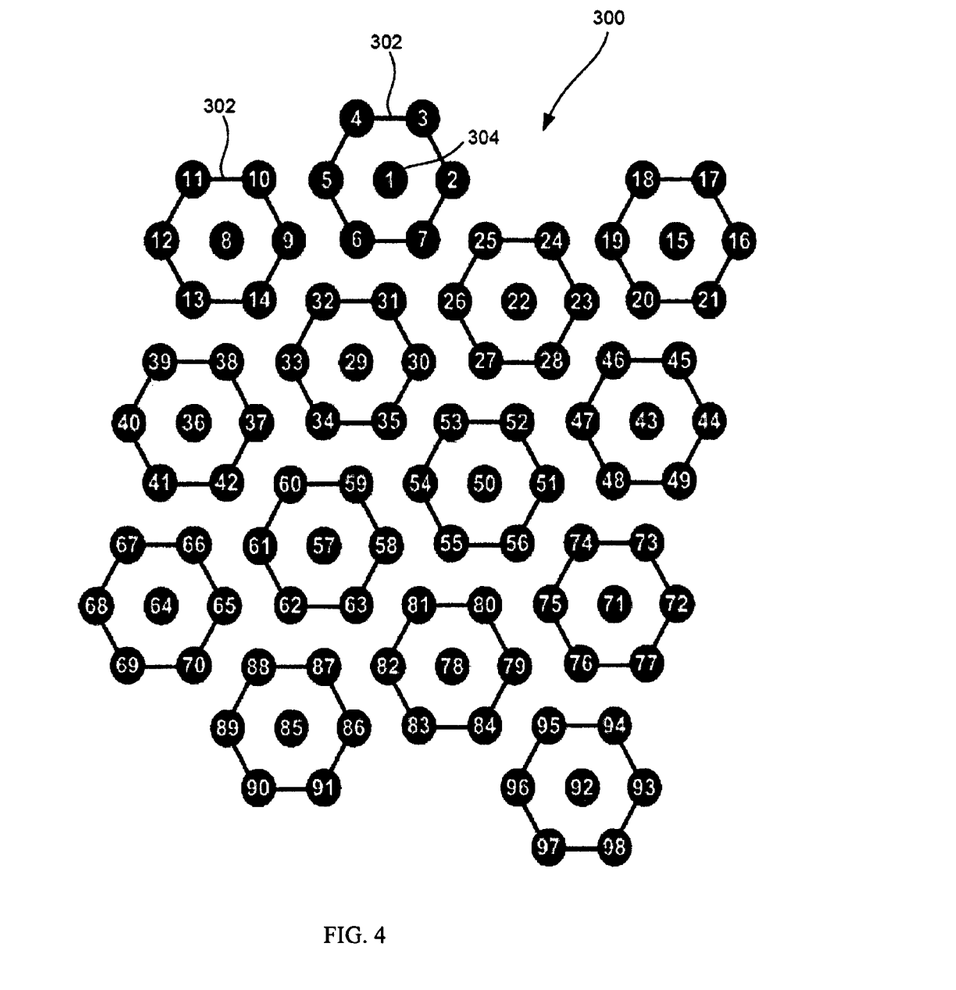
FIG. 4 is a schematic representation of the electrode array of FIG. 3 with a superimposed hexagonal logical array used for addressing.

One method of addressing the electrodes, as described in U.S. patent application No. US2009/0287275, the contents of which are incorporated herein by reference, comprises using a superimposed logical array 300 as shown in FIG. 4. This scheme has the advantage of enabling individual electrodes to be addressed in parallel to facilitate parallel stimulation. Repeating regular patterns, here hexagonal shapes 302, are overlaid on the physical electrode array 200. Each of the hexagons 302 contains seven electrodes 202. A numbering scheme, for example that shown in FIG. 4, is used to specify the centre of each hexagon so that the centre of each hexagon is separated from the centres of the adjacent hexagons throughout the array. In the addressing scheme, a single stimulation identifier is used to specify the stimulating electrodes within a plurality of the hexagons. This provides an efficient system for addressing the electrode array.

The centre of each hexagon 302, for example electrode 304, serves as the stimulating electrode, and is associated with a power source that may be located in the electronics capsule 112. One, two or all of the immediately adjacent electrodes (the electrodes at the corners of the hexagons 302) and/or a distant monopolar return path electrode 116 serve as the electrical return path for the current stimulus. During the first phase of biphasic stimulus, the centre electrode 304 in the hexagon 302 is connected to the power sources associated with its respective hexagon. Return path electrodes are connected to either a supply voltage or to a current or voltage sink. During the second charge recovery phase of biphasic stimulation, the electrical connections of the centre electrode and the return path are reversed.

Figure 5:
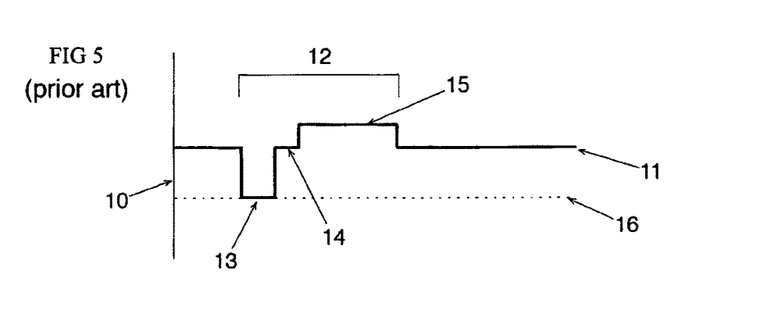
FIG. 5 depicts a biphasic electrical stimulus.

FIG. 5 shows a prior art biphasic electrical stimulus. The vertical axis 10 is the stimulus amplitude, which may be measured in units of current or voltage. The horizontal axis 11 is the time. The biphasic pulse 12 begins with a cathodic phase 13, followed by an optional inter-phase delay 14, then an optional anodic phase 15. Preferably, the anodic phase 15 should provide equal but opposite charge to the cathodic phase 13 to provide charge-recovery. In the present application, the inter-phase delay 14 and the anodic phase 15 are optional. The dashed line 16 is the threshold, namely, the stimulus amplitude at which the total charge delivered by the cathodic phase 13 would elicits response(s) from the stimulated cell(s). An alternative prior art biphasic pulse may begin with an anodic phase, followed by an optional inter-phase delay, then an optional cathodic phase, preferably of equal but opposite charge to the said anodic phase for charge-recovery. The cathodic phase 13 and anodic phase 15 may be asymmetric. In the general form, and for the methods described herein, the phases of a biphasic pulse need not be rectangular, as in FIG. 5. Instead, a cathodic phase 13 is to be understood as any pulse waveform that provides net cathodic charge; similarly, an anodic phase 15 is to be understood as any pulse waveform that provides net anodic charge. For retinal stimulation, the duration of the cathodic phase 13 may be in the range 0.1-5 ms. The inter-phase delay 14 may be in the range 0-1 ms.

Figure 6:
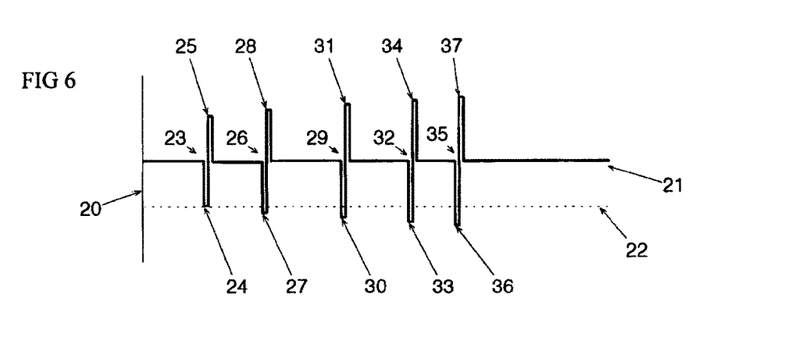
FIG. 6 depicts an example of a stimulation pattern for maintaining the responsiveness of excitable cells during repetitive stimulation.

FIG. 6 depicts a train of biphasic stimulus pulses configured for maintaining the evoked response reliably during repetitive electrical stimulation. The interval between biphasic stimulus pulses during repetitive electrical stimulation may be in the range 2-50 ms, for example. The vertical axis 20 is the pulse amplitude. The horizontal axis 21 is the time. The dashed line 22 represents the threshold for evoking response(s). Stimulation begins with a biphasic pulse 23, consisting of two phases, a cathodic phase 24 and an anodic phase 25. In each biphasic pulse, the cathodic phase may appear before the anodic phase, as in FIG. 6, alternatively the anodic phase may appear before the cathodic phase. For the purpose of illustration, in the following description and in FIG. 6, the cathodic phase appears before the anodic phase in all biphasic pulses. This should not be taken as a limiting requirement.

In order to elicit physiological response(s) in the stimulated cell(s), the charge of the cathodic phase 24 is preferably at, but could be above, threshold 22. To avoid electrode and tissue damage, the anodic phase 25 preferably delivers equal but opposite charge to the cathodic phase 24. Following this initial biphasic pulse 23, a series of biphasic pulses of monotonically increasing charge for the cathodic phase is delivered, namely a second biphasic pulse 26, a third biphasic pulse 29, a fourth biphasic pulse 32, and a fifth biphasic pulse 35. To maintain the responsiveness of the stimulated cell(s), the charge of the cathodic phase is progressively increased with each subsequent stimulus pulse. More specifically, the cathodic phase 27 charge of the second biphasic pulse 26 is greater than the cathodic phase 24 charge of the first biphasic pulse 23, the cathodic phase 30 charge of the third biphasic pulse 29 is greater than the cathodic phase 27 charge of the second biphasic pulse 26, the cathodic phase 33 charge of the fourth biphasic pulse 32 is greater than the cathodic phase 30 charge of the third biphasic pulse 29, and the cathodic phase 36 charge of the fifth biphasic pulse 35 is greater than the cathodic phase 33 charge of the fourth biphasic pulse 32. Preferably, the anodic phase of each biphasic pulse contains equal but opposite charge to the cathodic phase, to provide charge recovery. More specifically, the anodic phase 25 preferably contains equal but opposite charge to the cathodic phase 24, the anodic phase 28 preferably contains equal but opposite charge to the cathodic phase 27, the anodic phase 31 preferably contains equal but opposite charge to the cathodic phase 30, the anodic phase 34 preferably contains equal but opposite charge to the cathodic phase 33, and the anodic phase 37 preferably contains equal but opposite charge to the cathodic phase 36.

Referring to FIG. 6, in one arrangement the amplitude of the cathodic phase for each biphasic pulse is derived from the following mathematical equation:

$$I_n = I_0 \times 1 + [1-((1-\alpha) \times e^{-kn} + \alpha)] \quad \text{(Eq 1)}$$

where $I_n$ is the current amplitude to use for the cathodic phase of the n+1'th biphasic pulse, $I_0$ is the threshold current 22 for the first pulse 24, and a and k are the parameters that determine the magnitude of amplitude increase for each successive biphasic pulse in a pulse train. The choice of a and k is influenced by factors such as the stimulation frequency and the characteristics of the stimulated cell(s). In this arrangement, the value for a and k may be determined experimentally, such that minimal current increase is used to maintain the responsiveness of the cell(s) during repetitive stimulation. While this embodiment has been described with a specific mathematical equation with specific reference to the stimulus current amplitude and applications thereof, other mathematical equations that provide increasing $I_n$, and more generally, increasing phase charge, may be used.

In FIG. 6, the times between the biphasic pulses are not necessarily equal, but may be varied as needed in order to elicit the intended physiological responses in the stimulated cell(s). In each biphasic pulse, the anodic phase does not need to immediately follow a preceding cathodic phase. A brief inter-phase delay may be introduced as needed, in order to elicit the intended physiological responses in the stimulated cell(s).

In FIG. 6, it is to be understood that the use of five pulses per pulse train is for illustration only. The actual number of pulses per pulse train may be practiced otherwise than described herein and may vary from two upwards to an arbitrary number.

In practice, progressive increase of biphasic pulse phase charge cannot continue indefinitely, due to considerations such as stimulator compliance voltage, the electrode charge injection limits, or the dynamic range of the cellular response(s). Furthermore, many excitable cells operate with brief periods of activities, interleaved with phases of silence.

Figure 7:
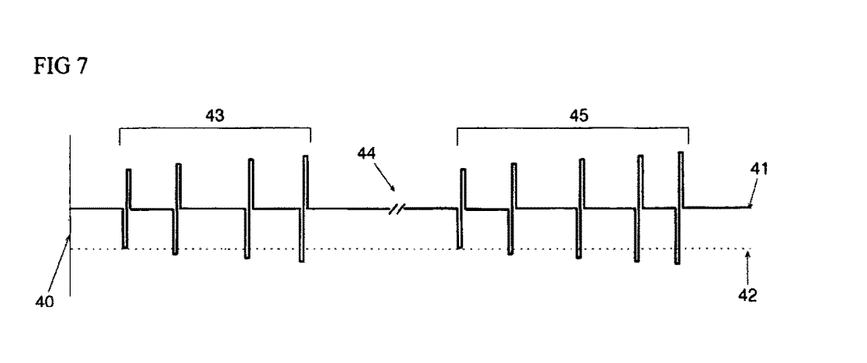
FIG. 7 depicts a further example of a stimulation pattern for maintaining the responsiveness of excitable cells during repetitive stimulation.

Referring to FIG. 7, the vertical axis 40 is the pulse current amplitude. The horizontal axis is the time 41. The dashed line 42 is the threshold for evoking response(s). Two pulse trains are generally shown, namely the first pulse train 43 and the second pulse train 45. These two pulse trains are separated by a quiescent period of time without electrical stimulus 44. The use of four biphasic pulses for the first pulse train 43 and five biphasic pulses for the second pulse train 45 are for illustration only. Other numbers may be used. There may, for example be between 2 and 20 stimulating pulses in each of the pulse trains 43, 45. The duration of the first pulse train is thus greater than around 2.2 ms (for example if there are two 0.1 ms monophasic pulses separated by 2 ms). After the quiescent period 44, the pulse current amplitude is reduced to an initial value and then increases monotonically during the second pulse train 45. The quiescent period 44 may last for 50 ms or more.

In an alternative implementation, each stimulating signal is encoded as a burst of pulses. The number of pulses in a specified time interval defines the strength of the stimulating signal. If the stimulation is to be repeated, the strength of the stimulating signal may be progressively increased by increasing the number of individual pulses in the specified time interval. The total charge delivered to the cell increases for each repetition of the stimulus, thereby maintaining the responsiveness of the cell. In one arrangement the pulses each have the same amplitude and form, although the method may also be implemented with bursts of pulses having different amplitudes and widths.

Figure 8:
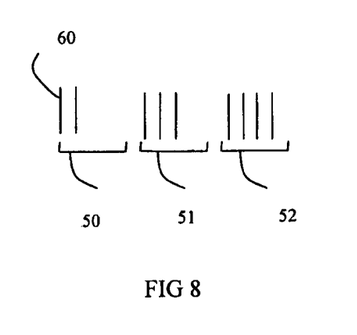
FIG. 8 is a schematic illustration of a stimulation pattern in which stimulation signal strength is varied by changing a number of pulses.

This method for varying signal strength is illustrated schematically in FIG. 8, which shows three stimulating signals applied in three sequential time intervals 50, 51, 52. In the first time interval 50 the stimulating signal has two pulses 60 having the same amplitude. Each pulse may be biphasic. In the second time interval 51 the stimulating signal has three pulses and in the third time interval 52 the stimulating signal has four pulses.

Calibrating the Monotonic Increase in Signal Strength

The strength of stimulating signals is progressively increased to offset fading of response that occurs in the cells on repeated stimulation. The increase in signal strength may be calibrated to match the fading of response. This calibration may, for example, be conducted during fitting of a retinal prosthesis. For example, the values of a and k in Eq. 1 for an implanted device in human patients may be determined through psychophysical experiments. For instance, the values of a and k may be varied while asking the subject to assess whether the artificially evoked responses were successfully maintained during repeated stimulation. Alternatively, or in conjunction with the foregoing approach, if the cellular responses of the stimulated cell(s) can be determined during electrical stimulation, then the responsiveness of these cells may be used to find the values of a and k, which maintain the responsiveness of these cells.

Figure 9:
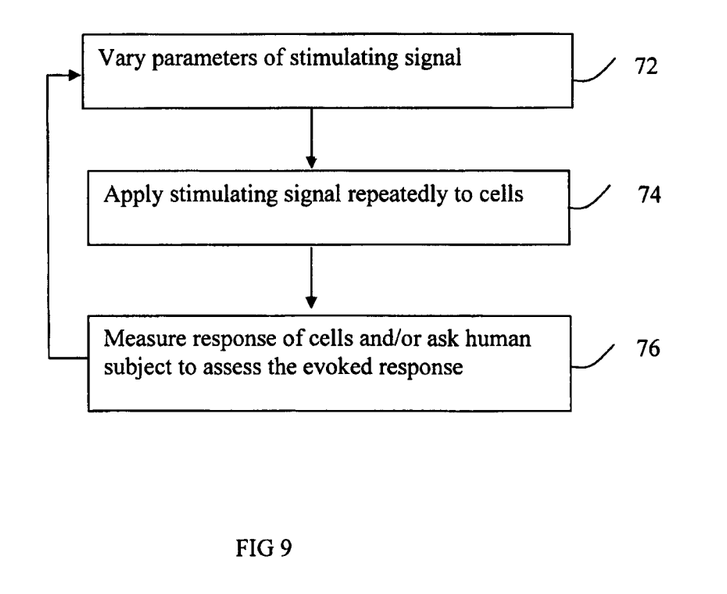
FIG. 9 is a flow chart of a method for calibrating parameters for the stimulation pattern for maintaining the responsiveness of excitable cells during repetitive stimulation.

This is illustrated in FIG. 9, which shows a flow chart of a method for calibrating the parameters of the increase in signal strength needed for repeated electrical stimulation. In step 72 the parameters (for example a and k) are set. This could be according to a programmed schedule, or could be determined by a person conducting a fitting of the retinal prosthesis. In step 74 the patient's cells are repeatedly stimulated using the parameters set in step 72. In step 76 the response of the cells is measured (if the measurements are available). Alternatively or in addition, the patient may be asked to assess the persistence of the evoked response at the current parameter settings. The method may be repeated to assess appropriate parameter settings for the patient.

It will be understood that the invention disclosed and defined in this specification extends to all alternative combinations of two or more of the individual features mentioned or evident from the text or drawings. All of these different combinations constitute various alternative aspects of the invention.

What is claimed is:

1. A method of neural stimulation, comprising:
applying a stimulating signal to electrically excitable cells to evoke a response from the electrically excitable cells; and
repeating the application of the stimulating signal with a progressively increasing signal strength by increasing a total electric charge applied to the cells per application to offset fading of response that occurs in the cells on repeated stimulation, wherein the progressively increasing signal strength is based on one or more of: (i) an earlier conducted calibration that assesses whether responses were successfully maintained during repeated application of the stimulating signal, and (ii) feedback of responses of the electrically excitable cells determined during repeated application of the stimulating signal.

2. A method according to claim 1 wherein increasing the signal strength comprises increasing an amplitude of the stimulating signal.

3. A method according to claim 1 wherein increasing the signal strength comprises increasing a pulse duration of the stimulating signal.

4. A method according to claim 1 wherein increasing the signal strength comprises increasing a number of pulses applied within a specified time period.

5. A method according to claim 1, further comprising:
interleaving repeated applications of the progressively increasing stimulating signal with a quiescent period.

6. A method according to claim 5 wherein the signal strength is reset to an initial value following the quiescent period.

7. A method according to claim 1 wherein the stimulating signal comprises a biphasic pulse having two phases of opposite charge.

8. A method according to claim 7 wherein increasing the signal strength comprises increasing an electric charge of each of the two phases.

9. A method according to claim 7 wherein the two phases of the biphasic pulse are separated by an inter-phase delay.

10. A method according to claim 7 wherein an anodic phase of the biphasic pulse contains a substantially equal and opposite charge to a cathodic phase of the biphasic pulse.

11. A method according to claim 1 wherein one or more parameters define a progression of the progressively increasing signal strength, wherein the earlier conducted calibrating adjusts the one or more parameters to offset the fading of response that occurs in the cells on repeated stimulation.

12. A method according to claim 11 wherein said calibrating comprises:
initialising the one or more parameters;
repeatedly applying the stimulating signal using the one or more parameters;
measuring a response of the cells to the repeated stimulation; and
adjusting the one or more parameters if the response of the cells varies with repeated stimulation.

13. A method according to claim 11 wherein said calibrating comprises:
initialising the one or more parameters;
repeatedly applying the stimulating signal to the cells of a human subject using the one or more parameters;
eliciting an assessment of an evoked response from the human subject; and
adjusting the one or more parameters if the elicited assessment indicates a variation in response of the cells with repeated stimulation.

14. A method according to claim 1 further comprising detecting sensory information, wherein the stimulating signal applied to the electrically excitable cells is dependent on the detected sensory information.

15. A method according to claim 14 wherein the electrically excitable cells comprise retinal neurons and detecting sensory information includes detecting image data.

16. A method according to claim 1 wherein the signal strength of the delivered electric charge within each pulse train increases progressively from the earlier portion of t pulse train to the later portion of the pulse train.

17. A method according to claim 1 wherein:
a first and a second of the two or more pulse trains are separated by a first quiesc period of time; and
the plurality of electrical pulses within each pulse train is separated by at least a second quiescent period of time that is less than the first quiescent period of time.

18. A method of retinal stimulation comprising:
detecting image data;
applying a stimulating signal to electrically excitable retinal cells to evoke a response from the retinal cells, wherein the stimulating signal is dependent on the detected image data; and
repeating the application of the stimulating signal with a progressively increasing signal strength by increasing a total electric charge applied to the retinal cells per application to offset fading of response that occurs in the cells on repeated stimulation.

* * * * *

UNITED STATES PATENT AND TRADEMARK OFFICE
CERTIFICATE OF CORRECTION

PATENT NO.       : 9,669,213 B2
APPLICATION NO.  : 13/981584
DATED            : June 6, 2017
INVENTOR(S)      : Tsai et al.

It is certified that error appears in the above-identified patent and that said Letters Patent is hereby corrected as shown below:

In the Claims

Claim 16, Column 8, Lines 31-32, please delete "of t pulse" and insert --of the pulse--;

Claim 17, Column 8, Line 35, please delete "first quiesc period" and insert --first quiescent period--.

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*